(12) United States Patent
Poundarik et al.

(10) Patent No.: US 12,274,809 B2
(45) Date of Patent: Apr. 15, 2025

(54) BIOMIMETIC NANO-COMPOSITE SCAFFOLD FOR ENHANCED BONE HEALING AND FRACTURE REPAIR

(71) Applicant: RENSSELAER POLYTECHNIC INSTITUTE, Troy, NY (US)

(72) Inventors: Atharva Abhay Poundarik, Troy, NY (US); Marta Monteiro Silva Carvalho, Lisbon (PT); Deepak Vashishth, Glenmont, NY (US)

(73) Assignee: RENSSELAER POLYTECHNIC INSTITUTE, Troy, NY (US)

( * ) Notice: Subject to any disclaimer, the term of this patent is extended or adjusted under 35 U.S.C. 154(b) by 173 days.

(21) Appl. No.: 15/570,942

(22) PCT Filed: May 2, 2016

(86) PCT No.: PCT/US2016/030410
§ 371 (c)(1),
(2) Date: Oct. 31, 2017

(87) PCT Pub. No.: WO2016/179089
PCT Pub. Date: Nov. 10, 2016

(65) Prior Publication Data
US 2018/0280570 A1 Oct. 4, 2018

Related U.S. Application Data

(60) Provisional application No. 62/290,628, filed on Feb. 3, 2016, provisional application No. 62/155,684, filed on May 1, 2015.

(51) Int. Cl.
*A61L 27/26* (2006.01)
*A61F 13/00* (2006.01)
(Continued)

(52) U.S. Cl.
CPC .............. *A61L 27/26* (2013.01); *A61F 13/00* (2013.01); *A61F 13/00063* (2013.01);
(Continued)

(58) Field of Classification Search
None
See application file for complete search history.

(56) References Cited

U.S. PATENT DOCUMENTS 6,319,934 B1 11/2001 Wagle et al.
6,384,194 B1 5/2002 Weis et al.
(Continued)

FOREIGN PATENT DOCUMENTS

CN 101584884 A 11/2009
NZ 579466 A 8/2012
(Continued)

OTHER PUBLICATIONS

Kim et al. Tissue Engineering: Part B, 2010;16(5)520-539). (Year: 2010).*
(Continued)

*Primary Examiner* — Evelyn Y Pyla
(74) *Attorney, Agent, or Firm* — Barclay Damon, LLP; Anthony P. Gangemi

(57) ABSTRACT

Provided is a method of mineralizing tissue, including placing within a body of a subject a substance, wherein the substance includes osteopontin and osteocalcin. Also provided is a tissue mineralization-promoting substance including osteopontin and osteocalcin, and an article for promoting tissue mineralization, including an implant which may be an orthopedic implant or an endosseous implant, and a substance disposed on a surface of the implant including osteopontin, and osteocalcin. A method of making a tissue mineralization-promoting substance, including combining osteopontin and osteocalcin, is also provided. Other fea-
(Continued)

tures, including calcium phosphate, type-I collagen, mesenchymal stem cells, and growth factors, are also provided.

8 Claims, 10 Drawing Sheets

(51) Int. Cl.
    *A61L 27/12* (2006.01)
    *A61L 27/46* (2006.01)
    *A61L 27/54* (2006.01)

(52) U.S. Cl.
    CPC .............. *A61L 27/12* (2013.01); *A61L 27/46* (2013.01); *A61L 27/54* (2013.01); *A61L 2300/414* (2013.01); *A61L 2300/64* (2013.01); *A61L 2430/02* (2013.01)

(56) References Cited

U.S. PATENT DOCUMENTS

| | | | |
|---|---|---|---|
| 6,509,026 | B1 | 1/2003 | Ashkar et al. |
| 7,544,496 | B2 | 6/2009 | Gower et al. |
| 7,718,168 | B2 | 5/2010 | Griffin et al. |
| 8,802,115 | B2 | 8/2014 | Altschuler et al. |
| 8,808,752 | B2 | 8/2014 | Oshima |
| 8,936,805 | B2 | 1/2015 | Biris |
| 9,005,646 | B2 | 4/2015 | Masinaei et al. |
| 2004/0131562 | A1 | 7/2004 | Gower et al. |
| 2005/0217538 | A1 | 10/2005 | Reinstorf et al. |
| 2006/0105013 | A1* | 5/2006 | Ashkar .................. C07K 14/52 424/423 |
| 2006/0286144 | A1 | 12/2006 | Yang et al. |
| 2007/0071728 | A1 | 3/2007 | Ko et al. |
| 2007/0248575 | A1 | 10/2007 | Connor et al. |
| 2008/0033572 | A1 | 2/2008 | D'Antonio et al. |
| 2008/0305517 | A1 | 12/2008 | Griffin et al. |
| 2009/0012625 | A1 | 1/2009 | Ying et al. |
| 2010/0272693 | A1 | 10/2010 | Lee et al. |
| 2011/0129544 | A1 | 6/2011 | Miyazaki et al. |
| 2013/0310539 | A1 | 11/2013 | Bourne et al. |
| 2013/0315889 | A1* | 11/2013 | Haudenschild ......... A61L 27/58 424/94.4 |
| 2014/0147419 | A1 | 5/2014 | Novakovic et al. |

FOREIGN PATENT DOCUMENTS

| | | |
|---|---|---|
| WO | 99/33415 A1 | 7/1999 |
| WO | 2013191492 A1 | 12/2013 |
| WO | 2014147278 A1 | 9/2014 |
| WO | 2014159863 A1 | 10/2014 |
| WO | 2015007393 A1 | 1/2015 |

OTHER PUBLICATIONS

Jonge et al., Pharmaceutical Research, vol. 25, No. 10, Oct. 2008, pp. 2357-2365 (Year: 2008).*
Munisamy et al., Journal of Oral Implantology, vol. XXXIV/ No. Two/2008, pp. 67-75 (Year: 2008).*
Ahmad et al., PLoS ONE 8(9): e72128, 7 pages (2013) (Year: 2013).*
Patent Cooperation Treaty, Notification of Transmittal of the International Search Report and the Written Opinion of the International Searching Authority, or the Declaration for PCT/US2016/030410 mailed Aug. 5, 2016, 14 pages.
Kaartinen et al., "Cross-linking of Osteopontin by Tissue Transglutaminase Increases Its Collagen Binding Properties," Jan. 1999, pp. 1729-1735, The Journal of Biological Chemistry, vol. 274, No. 3.
Valcourt et al., "Non-Enzymatic Glycation of Bone Collagen Modifies Osteoclastic Activity and Differentiation," Dec. 2006, 33 pages, JBC Papers in Press (http://www.jbc.org/cgi/doi/10.1074jbc.M610536200).
Hu et al., "Strongly Bound Citrate Stabilizes th Apatite Nanocrystals in Bone," Dec. 2010, pp. 22425-22429, PNAS, vol. 107, No. 52 (www.pnas.org/cgi/doi/10.1073/pnas.1009219107).
Chen et al., "An Osteopontin—Integrin Interaction Plays a Critical Role in Directing Adipogensis and Osteogenesis by Mesenchymal Stem Cells," Feb. 2015, pp. 1-19 NIH Public Access, Author Manuscript.
OMICS eBooks Group, Editors: Panseri et al., "Biomimetic Approaches for Tissue Healing," May 2015, pp. 1-39, OMICS eBooks Group, Chapter: Drug Delivery Strategies for Bone Tissue Regeneration.
Higashikawa et al., "Enhanced Biological Activity of Polymeric Osteopontin," May 2017, pp. 2697-2701, Federation of European Biochemical Societies (FEBS) Letters, vol. 581.
Hankenson et al. "Extracellular Signaling Molecules to Promote Fracture Healing and Bone Regeneration," Sep. 2015, pp. 3-12, Advanced Drug Delivery Reviews, vol. 94.
Martino et al., "Extracellular Matrix-Inspired Growth Factor Delivery Systems for Bone Regeneration," Apr. 2015, pp. 41-52, Advanced Drug Delivery Reviews, vol. 94.
Zou et al., "Osteopontin Promotes Mesenchymal Stem Cell Migration and Lessons Cell Stiffness via Integrin β1, FAK, and ERK Pathways," 2013, pp. 455-462, Cell Biochem. Biophys., vol. 65.
Nilsson et al., "Osteopontin, a Key Component of the Hematopoietic Stem Cell Niche and Regulator of Primitive Hematopoietic Progenitor Cells," Aug. 2005, pp. 1232-1239, Bolld, vol. 106, No. 4.
Tellado et al., "Strategies to Engineer Tendon/Ligament-to-bone Interface: Biomaterials, Cells and Growth Factors," Mar. 2015, pp. 126-140, Advanced Drug Delivery Reviews, vol. 94.
Dorozhkin, "Calcium Orthophosphate Cements for Biomedical Application," Mar. 2008, pp. 3028-3057, Journal Mater. Science, vol. 43.
Zwanziger, "The Multielemental Analysis of Bone," 1989, pp. 195-232, Biological Trace Element Research, vol. 19.
Hempel, U., et al., "Proliferation and Differentiation of Osteoblasts on Biocement D Modified with Collagen Type I and Citric Acid," Journal of Biomedical Materials Research, Part B, pp. 130-143, Jun. 21, 2004.
Schneiders, W., et al., "Effect of modification of hydroxyapatite/collagen composites with sodium citrate, phosphoserine, phosphoserine/RGD-peptide and calcium carbonate on bone remodelling," Bone, vol. 40, Issue 4, pp. 1048-1059, Apr. 2007.
Rammelt, S., et al., "Osteocalcin enhances bone remodeling around hydroxyapatite/collagen composites," Wiley InterScience, vol. 10, pp. 284-294, Mar. 30, 2055.
Rodriguez, D.E., et al., "Multifunctional role of osteopontin in directing intrafibrillar mineralization of collagen and activation of osteoclasts," Acta Biomaterialia, vol. 10, Issue 1, pp. 494-507, Jan. 2014.
Hunter, G.K., "Role of Osteopontin in Modulation of Hydroxyapatite Formation," Calcif Tissue Int., vol. 93, pp. 348-354, Jan. 19, 2013.
Ngiam, M., et al., "The fabrication of nano-hydroxyapatite on PLGA and PLGA/collagen nanofibrous composite scaffolds and their effects in osteoblastic behavior for bone tissue engineering," Bone, vol. 45, pp. 4-16, Apr. 2009.
Rodrigues, C.V.M., et al., "Characterization of a bovine collagen-hydroxyapatite composite scaffold for bone tissue engineering," Biomaterials, vol. 24, pp. 4987-4997, May 30, 2003.

* cited by examiner

BIOMIMETIC NANO-COMPOSITE SCAFFOLD FOR ENHANCED BONE HEALING AND FRACTURE REPAIR

CROSS-REFERENCE TO RELATED APPLICATIONS

This application is a national stage filing under section 371 of International Application No. PCT/US2016/030410 filed on May 2, 2016, published in English on Nov. 10, 2016 as WO2016/179089A1, which claims priority under 35 U.S.C. § 119 to U.S. Provisional Application No. 62/155,684, filed May 1, 2015, and U.S. Provisional Application No. 62/290,628, filed Feb. 3, 2016, which are herein incorporated by reference in their entireties.

GOVERNMENT RIGHTS STATEMENT

This invention was made with government support under AR49635 awarded by the NIH and Award No. 1462613 awarded by the NSF. The government has certain rights in the invention.

FIELD OF THE INVENTION

The present invention relates to, inter alia, methods, substances, and articles for promoting mineralization of bone tissue. The invention includes implantable substances and articles, methods of their manufacture, and methods of promoting tissue mineralization, that may induce the repair or replacement of damaged or diseased bone or other tissue in vivo. The invention may facilitate adhesion and proliferation of bone cells and improve differentiation of osteoblasts and mineralization.

BACKGROUND OF THE INVENTION

Each year, bone fractures require millions of hospitalizations worldwide. An estimated 200 million women are at risk of bone fracture due to osteoporosis. Bone cancer treatment and bony fusions (spinal, cervical, ankle, etc.) also require restoration of a large volume of bone. In such cases, bone must be repaired or regenerated to fill in a defect and restore structure and function to damaged tissue. The high numbers of patients with bone fractures and defects that need regenerative treatment are a cause of socioeconomic concern, and this number is poised to increase in the next years due to an aging population.

Current medical treatments for severe bone injuries include autologous bone grafts or autografts (bone tissue obtained from the patient's body) to stimulate healing of skeletal fractures/defects. Autologous bone grafts provide osteogenic cells as well as osteoinductive stimuli needed for bone healing and regeneration. However, there are limited sites where bone maybe harvested without loss of function, leading to a limited amount of autograft that can be obtained. Autografting also has other complications such as pain, infection, scarring, blood loss and donor-site morbidity. Allogeneic demineralized bone grafts, derived from cadavers, are an alternative in bone reconstructive surgery but lack bone growth-inducing factors necessary for efficacy. This approach also has other important limitations including higher risk of immunologic rejection and infection.

Some materials have been used in bone repair without great success, such as metals and ceramics. Metals may be permanently placed in bone to fill a defect and provide internal fixation but fatigue, corrosion, tissue infection, and poor implant-tissue interface can give rise to many problems for patients. Due to the greater mechanical properties of metals than natural bone, stress-shielding effect can occur, causing bone resorption around the implant, and it may require the removal of the implant. Synthetics such as calcium phosphates or other ceramics, and their composites with biomolecules like collagen, may be used based on the fact that their composition is similar to the composition of bone, thereby offering biocompatibility. However, such materials cannot provide structural support to load-bearing bones and lack the efficacy of the autograft.

Thus, improvements in bone tissue engineering are needed to provide promising solutions for reconstructing bone tissue and new and effective strategies that avoid the need for autografts or allografts but without the limitations and drawbacks of current treatments.

SUMMARY OF THE INVENTION

The present invention relates to, inter alia, a method of mineralizing tissue, including placing within a body of a subject a substance, wherein the substance includes type I collagen, calcium phosphate, osteopontin, and osteocalcin.

In another aspect, the present invention includes a tissue mineralization-promoting substance including type-I collagen, calcium phosphate, osteopontin, and osteocalcin.

In another aspect, the present invention includes an article for promoting tissue mineralization, including an implant which may be an orthopedic implant or an endosseous implant, and a substance disposed on a surface of the implant, and the substance includes type I collagen, calcium phosphate, osteopontin, and osteocalcin.

In another aspect, the present invention includes a method of making a tissue mineralization-promoting substance, including combining calcium, phosphate, type-I collagen, osteopontin, and osteocalcin.

In another aspect, the present invention includes a method of making a tissue mineralization-promoting substance, including contacting a solid template including type I collagen with calcium, phosphate, osteopontin, and osteocalcin.

In another aspect, the present invention includes a method of mineralizing tissue, including placing within a body of a subject a substance, and the substance includes osteopontin, osteocalcin, and a carrier.

In another aspect, the present invention includes a tissue mineralization-promoting substance, including osteopontin, osteocalcin, and a carrier.

In another aspect, the present invention includes an article for promoting tissue mineralization, including an orthopedic implant or an endosseous implant, and a substance disposed on a surface of the implant, the substance including osteopontin, osteocalcin, and a carrier.

In another aspect, the present invention includes a method of making a tissue mineralization-promoting substance, including combining osteopontin, osteocalcin, and a carrier.

In another aspect, the present invention includes a method of making a tissue mineralization-promoting substance, including contacting a solid template with osteopontin and osteocalcin.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements. The foregoing and other objects, features, and advantages of the invention are apparent from the following detailed description taken in conjunction with the accompanying drawings in which.

DETAILED DESCRIPTION OF THE INVENTION

Figure 1:
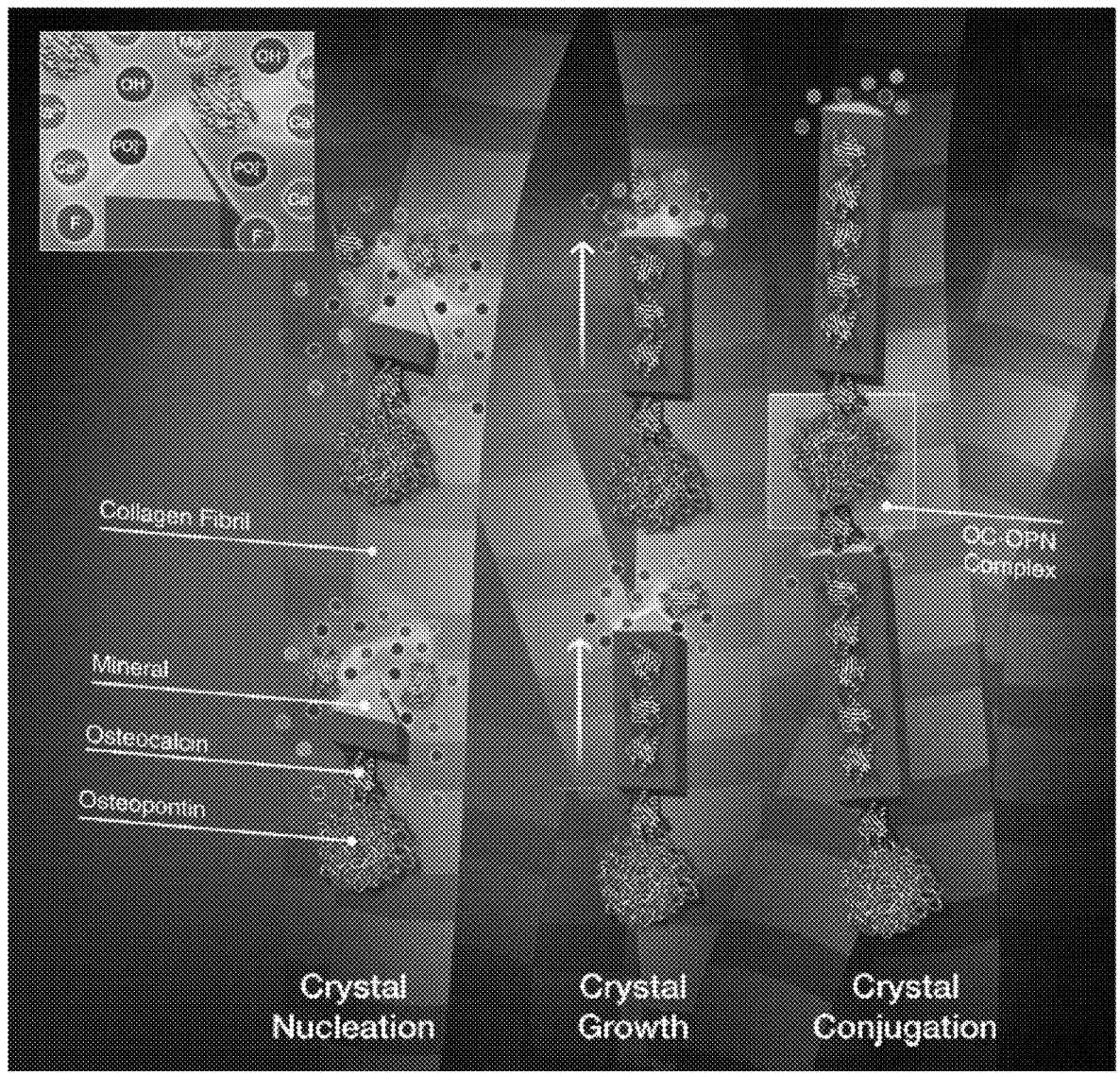
FIG. 1 is a representative illustration showing interactions between osteopontin, osteocalcin, collagen, and mineral in processes of bone regeneration and mineralization, including crystal nucleation, crystal growth, and crystal conjugation.

Aspects of the present invention and certain features, advantages, and details thereof, are explained more fully below with reference to the non-limiting embodiments illustrated in the accompanying drawings. Descriptions of well-known materials, fabrication tools, processing techniques, etc., are omitted so as to not unnecessarily obscure the invention in detail. It should be understood, however, that the detailed description and the specific examples, while indicating embodiments of the invention, are given by way of illustration only, and are not by way of limitation. Various substitutions, modifications, additions and/or arrangements within the spirit and/or scope of the underlying inventive concepts will be apparent to those skilled in the art from this disclosure.

Following are various, optional, non-limiting examples of combinations, some including individual features, such combinations and features which may each represent non-limiting embodiments of an invention disclosed herein. In no case is a description of any particular combination or inclusion of a feature a representation that any invention disclosed herein is limited to such combination or requires inclusion of any such feature absent an explicit statement to the contrary.

The present invention includes a method of mineralizing tissue, including placing within a body of a subject a substance that includes type I collagen, calcium phosphate, osteopontin, and osteocalcin. In one aspect of this method, calcium phosphate may be selected from any of various types of calcium phosphate known to be suitable for bone mineralization, including monocalcium phosphate monohydrate, monocalcium phosphate anhydrous, dicalcium phosphate dihydrate, dicalcium phosphate anhydrous, octacalcium phosphate, α-tricalcium phosphate, β-tricalcium phosphate, amorphous calcium phosphate, calcium-deficient hydroxyapatite, hydroxyapatite, fluorapatite, tetracalcium phosphate, or any combination of two or more of the foregoing. See Dorozhkin (2008), J. Mater. Sci., 43:3028-3057. Any combination of any of the foregoing types of calcium phosphate is explicitly intended as part of the present invention.

In another aspect of this method, the substance may include a coating on an implant, a gel, a granular substance, a paste, a cement, or a liquid. Various such substances, for use in promoting bone regeneration, tissue mineralization, bone repair, etc., are well-known in the relevant field and would be readily recognized by skilled artisans as adaptable for use in accordance with the present invention. In some embodiments, the substance may be applied as more than one of these examples while remaining within the present invention as disclosed herein. Any of the calcium phosphate examples identified above, alone or as combined, is explicitly included along with any of the foregoing examples of substances, or any others, as embodiments of the present invention.

In another aspect of this method, the substance may include a scaffold, which may be, as one non-limiting example, a pre-fabricated collagen/carrier matrix, and/or a plurality of cells disposed on the scaffold. The cells may include any type or combination of types of cells known to play a role in bone regeneration, growth, repair, and tissue mineralization. For example, the plurality of cells may include osteoblasts, osteoclasts, fibroblasts, mesenchymal stem cells, embryonic stem cells, and any combination of two or more of the foregoing. Any single example or any combination of more than one of these examples may be included within the invention as disclosed herein. Also, any one or more of the examples of calcium phosphate described above may be used with scaffolds and/or such cells in accordance with the present invention, and every combination thereof is explicitly included herein.

In another aspect, this method may include a substance with one or more compounds known in the art to promote bone regeneration, healing, or tissue mineralization, such as minerals or other trace elements found in bone or used in attempts to repair or heal bone or mineralize tissue, such as magnesium, sodium, fluorine, chlorine, sulfur, zinc, iron, silicon, selenium, strontium, copper, lithium, nickel, manganese, barium, phosphorous, aluminum, cobalt, titanium, vanadium, and any combination of two or more of the foregoing. See Zwanziger (1989) Biological Trace Elements Research, 19:195-232. All of the foregoing examples of compounds may be included within a substance as part of this method. These compounds or any one or combination thereof may be used with any of the types and combinations of calcium phosphate discussed above, as well as any of the types or combinations of substances and/or cells described above. Every combination of calcium phosphate, substance and types of substances, cell type, and compound described above is hereby explicitly included as examples of the present method.

In another aspect of this method, the substance may include osteopontin or osteocalcin molecules, or both, cross-linked to collagen, or to each other, or all of the above. Numerous cross-linking agents are suitable for cross-linking osteopontin, osteocalcin, and/or collagen to each other are known to skilled artisans. One non-limiting example is the enzyme transglutaminase 2, but others may be used and are also understood as being in accordance with the present invention. Osteopontin, osteocalcin, and/or collagen cross-linked to each other as described may be combined with any of the types or combinations of calcium phosphate, substances, cells, and/or compounds disclosed above. Such combinations are explicitly included as aspects of the present method.

In another aspect the present method includes contacting the substance with a compound that inhibits the formation of advanced glycation endproducts (AGEs) and/or non-enzymatic cross-links, or removes AGEs and/or non-enzymatic cross-links. Any compound or compounds known in the art to be capable of inhibiting and/or removing such AGEs and non-enzymatic cross-links could be used in accordance with this aspect of the present method, including 3-phenacyl-4,5-dimethylthiazolium chloride, ALT-462, ALT-486, ALT-946, N-phenacylthiazolium bromide, 4,5-dimethyl-3-phenylacylthiazolium chloride, TRC4186, TRC4149, C36, C16, L-bis-4[-(4-benzamidophenoxyisobutyryl)cystine], 4-(3,5-dichlorophenylureido)-phenoxyisobutyryl-1-aminocyclohexane-1-carboxylic acid, 4-[(3,5-dichlorophenylureidophenoxyisobutyryl]-4-aminobenzoic acid), 1,4-benzene-bis[4-methylene-aminophenoxyisobutyric acid], 5-aminosalicylic acid, dimethylbiguanide, methylene bis[4,4'-(2-chlorophenylureidophenoxyisobutyric acid, benfotiamine, pyridoxamine, pimagedine, alpha-lipoic acid, taurine, aspirin, carnosine, desferrioxamine, penicillamine, pioglitazone, pentoxyfylline, metformin, 2-isopropylidenehydrazono-4-oxo-thiazolidin-5-ylacetinilide, 2,3-diaminopropionic acid, amadorins, yruvate, nicartinitine, losartan, 4-(2-naphtylcarboxamido)phenoxyisobutyric acid, 4-(2-chloro-4-nitrophynylureido) phenoxyisobutyric acid, 4-[(3,4-dichlorophenylmethyl) 2-chlorophenylureido]phenoxyisobutyric acid, 4-(2,4-dichlorophenacylamino)phenoxyisobutyric acid, and/or 2-(8-quinolinoxy)propionic acid. See U.S. Pat. No. 9,309,304 to Bourne. Any one or combination of two or more of any and all of these agents may be used in accordance with the present invention and all such compounds and possible combinations thereof are hereby explicitly stated as examples of the present method. Any of the exemplary types or combination of calcium phosphate, substances and types of substances, cells, compounds, and/or osteopontin and/or osteocalcin cross-linked to each-other and/or to collagen, together with any of the types of compounds identified herein that inhibit non-enzymatic cross-linking of collagen fibrils or removes cross-links between collagen fibrils or combinations thereof are hereby explicitly included as examples contemplated as included within the present invention and method. This method also includes rinsing or washing any AGE/nonenzymatic cross-link inhibitor/remover compound or compounds from the substance before placing the substance within a body of a subject.

In another aspect of this method, the substance includes one or more growth factors known to those possessing skill in the art relevant to the present invention to promote bone regeneration and healing and tissue mineralization. See Martino et al. (2015) Adv. Drug. Discovery Rev., 94:41-52; Tellado et al., (2015), Adv. Drug. Discovery Rev., 94:126-140; Hankenson et al., (2015) Adv. Drug. Discovery Rev., 94:3-12. Examples may include a platelet-derived growth factor, a bone morphogenetic protein, an insulin-like growth factor, a transforming growth factor-$\beta$, a vascular endothelial growth factor, a fibroblast growth factor, and any combination of two or more of the foregoing. Any of the foregoing or any combination thereof may be included and is explicitly stated as an example of the present method and invention. Any one or combination of the foregoing growth factors may be used, in combination with any type or combination of calcium phosphate, substances, cells, compounds, and/or osteopontin and/or osteocalcin cross-linked to each-other and/or to collagen, and agent or agents to prevent, inhibit, or remove AGEs or non-enzymatic cross-linking of collagen, which optionally may be washed from a substance before placing it within the body of a subject, and all such combinations are hereby explicitly included as examples within the present invention and method.

In another aspect of the present invention, placing within a body of a subject a substance in accordance with the present invention and method includes injecting, implanting, disposing in a void within a bone, disposing between bones, disposing in cartilage, disposing on a surface of a bone or interface between soft tissue such as ligament, tendon, or cartilage and bone, screwing into a bone, implanting in a bone, or pinning in a bone. Each of these methods of placing a substance, alone and in combination with each and every of the other examples, is included in the present method and invention. Any one or combination of the foregoing methods of placing a substance may be used in accordance with and are part of the present invention, along with any type or combination of foregoing growth factors, calcium phosphate, substances, cells, compounds, and/or osteopontin and/or osteocalcin cross-linked to each-other and/or to collagen, and agent or agents to prevent, inhibit, or remove AGEs or non-enzymatic cross-linking of collagen (which optionally may be washed from a substance before placing it within the body of a subject) disclosed above, and all such combinations are hereby explicitly included as examples within the present invention and method.

For each and every example and combination of examples disclosed above, the subject may be any vertebrate, including fish, amphibian, reptile, bird, or mammal, including pig, cow, horse, sheep, dog, cat, mouse, rat, or any human or non-human primate.

In another aspect of the present invention and this methodological embodiment, the substance may optionally include a proportion by weight of collagen of between 20% and 80% and a proportion by weight of calcium phosphate of between 20% and 80%. Different relative proportions of collagen and calcium phosphate may be selected based on factors known to skilled artisans to be influenced by such proportions, such as degree of tissue mineralization attained by applying the substance, and hardness, brittleness, and flexibility of bone achieved, as well as attempts to induce such qualities in a manner to comport with the purpose, place, or tissue for or in which such substance is disposed. A substance may be approximately 20%, 25%, 30%, 35%, 40%, 45%, 50%, 55%, 60%, 65%, 70%, 75%, or 80% by weight collagen and approximately 20%, 25%, 30%, 35%, 40%, 45%, 50%, 55%, 60%, 65%, 70%, 75%, or 80% by weight calcium phosphate, or ranges in between these values, all of which are explicitly stated and herein included as examples of the present invention. Each of these relative concentrations by weight of collagen and calcium phosphate may be combined with any of the methods of placing a substance, type or combination of growth factors, calcium phosphate, substances, cells, compounds, and/or osteopontin and/or osteocalcin cross-linked to each-other and/or to collagen, and agent or agents to prevent, inhibit, or remove AGEs or cross-linking of collagen (which optionally may be washed from a substance before placing it within the body of a subject), and with any of the subjects, disclosed above, and all such combinations are hereby explicitly included as examples within the present invention and method.

In another aspect of the present invention and this methodological embodiment, the substance optionally further includes citrate. Citrate ions have a tridentate structure that is similar to osteocalcin's hydroxyapatite's binding motif and is thus postulated to attach to mineral surface and maximize its interfacial stability. See Hu et al. (2010), Proceedings of the National Academy of Sciences, 107: 22425-22429. Thus, citrate may be added to the substance in accordance with the present invention and methodological embodiment of promoting mineralization. Citrate may be included in combination with any of the relative concentrations by weight of collagen and calcium phosphate, methods of placing a substance, type or combination of growth factors, calcium phosphate, substances, cells, compounds, and/or osteopontin and/or osteocalcin cross-linked to each-other and/or to collagen, and agent or agents to prevent, inhibit, or remove AGEs or non-enzymatic cross-linking of collagen (which optionally may be washed from a substance before placing it within the body of a subject) disclosed above, and all such combinations are hereby explicitly included as examples within the present invention and method.

In another embodiment, the present invention includes a tissue mineralization-promoting substance, including type I collagen, calcium phosphate, osteopontin, and osteocalcin. In this aspect, the substance may share any and all of the possible foregoing characteristics of such a substance used in the method of mineralizing tissue described above. It would be understood by those with skill in the relevant field that any one or some or all of the potential combinations of factors and features used in a substance as described above (e.g., types of calcium phosphate, types of substances, types of cells disposed on a scaffold, minerals or other trace elements found in bone or used in attempts to repair or heal bone or mineralize tissue, osteopontin or osteocalcin molecules, or both, cross-linked to collagen, or to each other, or all of the above, an agent or agents that prevent, inhibit, or remove AGEs or non-enzymatic cross-linking of collagen fibrils, growth factors, relative proportions by weight of collagen and calcium phosphate, and/or citrate) with regard to the aforedescribed methodological embodiment of the present invention may likewise be included within the embodiment of the present invention as a mineralization-promoting substance. All such combinations are explicitly considered and included as optional examples of the present invention.

In another embodiment, the present invention includes an article for promoting tissue mineralization. The article may include, for example, an implant, wherein the implant is an orthopedic implant or an endosseous implant, and a substance disposed on a surface of the implant, wherein the substance comprises type I collagen, calcium phosphate, osteopontin, and osteocalcin. It would be understood by those with skill in the relevant field that each and any one or some or all of the potential combinations of factors and features optionally used in a substance as described above (e.g., types of calcium phosphate, types of substances, types of cells disposed on a scaffold, minerals or other trace elements found in bone or used in attempts to repair or heal bone or mineralize tissue, osteopontin or osteocalcin molecules, or both, cross-linked to collagen, or to each other, or all of the above, an agent or agents that prevent, inhibit, or remove AGEs or non-enzymatic cross-linking of collagen fibrils, growth factors, relative proportions by weight of collagen and calcium phosphate, and/or citrate) with regard to the aforedescribed methodological embodiment of the present invention and embodiment of the present invention as a tissue-promoting substance may likewise be included within the instant embodiment of the present invention as an article for promoting tissue-mineralization. All such combinations are explicitly considered and included as optional examples of the present invention.

In another embodiment, the present invention includes a method of making a tissue mineralization-promoting substance, including combining calcium phosphate, type-I collagen, osteopontin, and osteocalcin. Calcium and phosphate could be provided together as one of the examples of calcium phosphate presented above or each provided as part of a chemical entity that is independent of the other to promote mineralization upon combination by performance of the method. It would be understood by those with skill in the relevant field that any one or some or all of the potential combinations of factors and features used in a substance as described above (e.g., adding minerals or other trace elements found in bone or used in attempts to repair or heal bone or mineralize tissue to the calcium, phosphate, type-I collagen, osteopontin, and osteocalcin, cross-linking osteopontin and/or osteocalcin molecules to collagen and/or to each other, adding to the calcium, phosphate, type-I collagen, osteopontin, and osteocalcin a compound that inhibits non-enzymatic cross-linking of collagen fibrils or removes cross-links between collagen fibrils and, optionally, washing such compound from the substance, adding a weight of collagen and a combined weight of calcium and phosphate such that the relative weight of collagen is anywhere between 20% and 80%, and a combined weight of calcium and phosphate is anywhere between 20% and 80%, of the combined weight of collagen, calcium, phosphate, osteocalcin, and osteopontin, forming the substance into any one or more of the types of substances identified above, disposing any one or more of the aforementioned cells on the substance, adding any type or combination of aforementioned growth factors, and/or citrate) with regard to the aforedescribed embodiments of the present invention may likewise be included within the instant embodiment of the present invention as a method for forming a substance for promoting tissue-mineralization. All such combinations are explicitly considered and included as optional examples of the present invention.

In another aspect of the present invention, a method of mineralizing tissue is provided, including placing a substance within a body and the substance includes osteocalcin, osteopontin, and a carrier. A carrier may be any material recognized by skilled artisans suitable for placement within a body to hold bioactive substances such as, as non-limiting examples, any proteins, peptides, minerals, and/or cells in or near a region of the body in which it is placed and create a source of release of such substances into surrounding tissue, a structural location for recruitment of endogenous factors within the body for promoting tissue mineralization, or some combination of both functions. See Panseri et al., "Drug Delivery Strategies for Bone Tissue Regeneration." Biomimetic Approaches for Tissue Healing, OMICS Group eBooks, 2015. Nonlimiting examples of possible carriers include poly(lactic) acid, polyglycolic acid, poly(lactic-co-glycolic) acid, polyethylene glycol, collagen, alginate, chitosan, dextran, chitin, fibrin, gelatin, hyaluronic acid, silk fibroin, a calcium phosphate ceramic, a bioactive glass, and any combination of two or more of the foregoing. All combinations of two or more such exemplary carriers are explicitly included as within the present invention and this embodiment. In this aspect, the substance of the instant methodological embodiment of the present invention may share one or some or all of the possible foregoing characteristics of such a substance used in the method of mineralizing tissue described above. It would be understood by those with skill in the relevant field that one or some or all of the relevant, potential combinations of factors and features used in a substance as described above (e.g., types of substances, types of cells disposed on a scaffold, minerals or other trace elements found in bone or used in attempts to repair or heal bone or mineralize tissue, osteopontin or osteocalcin molecules, or both, cross-linked to collagen, or to each other, or all of the above, a compound that inhibits non-enzymatic cross-linking of collagen fibrils or removes cross-links between collagen fibrils, growth factors, examples of ways to place the substance within the body of a subject, examples of types of subjects, and/or citrate) with regard to the aforedescribed methodological embodiment of the present invention may likewise be included within the instant embodiment of the present invention. All such combinations are explicitly considered and included as optional examples of the present invention.

In another embodiment, the present invention includes a tissue mineralization-promoting substance, including osteopontin, osteocalcin, and a carrier. In this aspect, the substance may share any and all of the relevant, possible foregoing characteristics of such a substance used in above-described substances in accordance with the present invention. It would be understood by those with skill in the relevant field that any one or some or all of the potential combinations of factors and features used in a substance as described above (e.g., types of carriers, types of substances, types of cells disposed on a scaffold, minerals or other trace elements found in bone or used in attempts to repair or heal bone or mineralize tissue, osteopontin or osteocalcin molecules, or both, cross-linked to collagen, or to each other, or all of the above, a compound that inhibits non-enzymatic cross-linking of collagen fibrils or removes cross-links between collagen fibrils, growth factors, and/or citrate) with regard to the aforedescribed embodiments of the present invention may likewise be included within the instant embodiment of the present invention as a tissue mineralization-promoting substance. All such combinations are explicitly considered and included as optional examples of the present invention.

In another embodiment, the present invention includes an article for promoting tissue mineralization. The article may include, for example, an implant, wherein the implant is an orthopedic implant or an endosseous implant, and a substance disposed on a surface of the implant, wherein the substance comprises osteopontin, osteocalcin, and a carrier. It would be understood by those with skill in the relevant field that each and any one or some or all of the relevant, potential combinations of factors and features optionally used in a substance as described above (e.g., types of carrier, types of substances, types of cells disposed on a scaffold, minerals or other trace elements found in bone or used in attempts to repair or heal bone or mineralize tissue, osteopontin or osteocalcin molecules, or both, cross-linked to collagen, or to each other, or all of the above, a compound that inhibits non-enzymatic cross-linking of collagen fibrils or removes cross-links between collagen fibrils, growth factors, and/or citrate) with regard to the aforedescribed embodiments of the present invention may likewise be included within the instant embodiment of the present invention as an article for promoting tissue-mineralization. All such combinations are explicitly considered and included as optional examples of the present invention.

In another embodiment, the present invention includes a method of making a tissue mineralization-promoting substance, including combining calcium, phosphate, type-I collagen, osteopontin, and osteocalcin. It would be understood by those with skill in the relevant field that any one or some or all of the potential combinations of factors and features used in a substance as described above (e.g., using identified type or types of carrier, adding minerals or other trace elements found in bone or used in attempts to repair or heal bone or mineralize tissue to the osteopontin, osteocalcin, and carrier, using type-I collagen as carrier and cross-linking osteopontin and/or osteocalcin molecules to the type-I collagen and/or to each other, using type-I collagen as carrier and adding to the substance a compound that inhibits non-enzymatic cross-linking of collagen fibrils or removes cross-links between collagen fibrils and, optionally, washing such compound from the substance, forming the substance into any one or more of the types of substances identified above, disposing any one or more of the aforementioned cells on the substance, adding any type or combination of aforementioned growth factors, and/or citrate) with regard to the aforedescribed embodiments of the present invention may likewise be included within the instant embodiment of the present invention as a method for forming a substance for promoting tissue-mineralization. All such combinations are explicitly considered and included as optional examples of the present invention.

In another embodiment, the present invention includes a method of making a tissue mineralization-promoting substance, including contacting a solid template with osteopontin and osteocalcin. A solid template may be any implant, carrier, or porous article recognized by those skilled in the art as suitable to provide support to mineralization-promoting features of the substance. Non-limiting examples of a solid template include a porous template, a sheet, or a sponge. A solid template may be suitable for placement within a body to hold bioactive substances such as proteins, peptides, minerals, and/or cells in or near a region of the body in which it is placed and create a source of release of such substances into surrounding tissue, a structural location for recruitment of endogenous factors within the body for promoting tissue mineralization, or some combination of both functions. A template may serve as a temporary support for growth or development of a tissue mineralization-promoting substance, optionally aided by the addition of cells or growth factors known to promote such development, with the substance to be removed or the template discarded allowing subsequent use of the substance. A solid template may include a carrier, such as any one or more of the carriers identified above. It would be understood by those with skill in the relevant field that any one or some or all of the potential combinations of factors and features used in a substance or method of making a substance as described above (e.g., carriers, adding minerals or other trace elements found in bone or used in attempts to repair or heal bone or mineralize tissue to the osteopontin, osteocalcin, and solid template, using type-I collagen as carrier and cross-linking osteopontin and/or osteocalcin molecules to the type-I collagen and/or to each other, using type-I collagen as carrier and adding to the substance a compound that inhibits non-enzymatic cross-linking of collagen fibrils or removes cross-links between collagen fibrils and, optionally, washing such compound from the substance, forming the substance into any one or more of the types of substances identified above, disposing any one or more of the aforementioned cells on the substance, adding any type or combination of aforementioned growth factors, and/or citrate) with regard to the aforedescribed embodiments of the present invention may likewise be included within the instant embodiment of the present invention as a method for forming a substance for promoting tissue-mineralization. All such combinations are explicitly considered and included as optional examples of the present invention.

Bone is a complex hierarchical material comprising collagen type-I, mineral and non-collagenous proteins. Collagen is a principal organic component in bone and imparts bone ductility. Mineral, present as hydroxyapatite (HA) stiffens bone matrix and makes it resistant to deformation. In accordance with the present invention, non-collagenous proteins osteocalcin and osteopontin serve multiple functions in promoting bone formation and tissue mineralization. In one aspect, as shown in FIG. 1, bone mineral crystals nucleate under the cooperative action of osteocalcin (OC) and osteopontin (OPN). The highly charged OPN aids in the recruitment of essential ionic groups and trace elements. OC regulates crystal growth along the long axis of collagen, by attaching at favorable crystallographic locations on the growing crystal. Finally, crystals conjugate with each other through the formation of OC-OPN linkages, when they arrive at another nucleation site. In accordance with the present invention, OC and OPN act synergistically, and unexpectedly, to promote proliferation of cells involved in bone formation, deposition of minerals involved in bone formation and tissue mineralization, and the formation, shape, size, and orientation of bone mineral. These synergistic effects, also surprisingly, occur by multiple processes, involving not only the functions illustrated in FIG. 1, aiding in the association and growth of mineral crystals along collagen fibrils, but also by direct biological effects on cells, independent of these structural roles. A bone graft, in accordance with the present invention, addresses challenges currently faced in the treatment of bone fractures and defects by employing these newly discovered properties of OC and OPN.

Figure 2A:
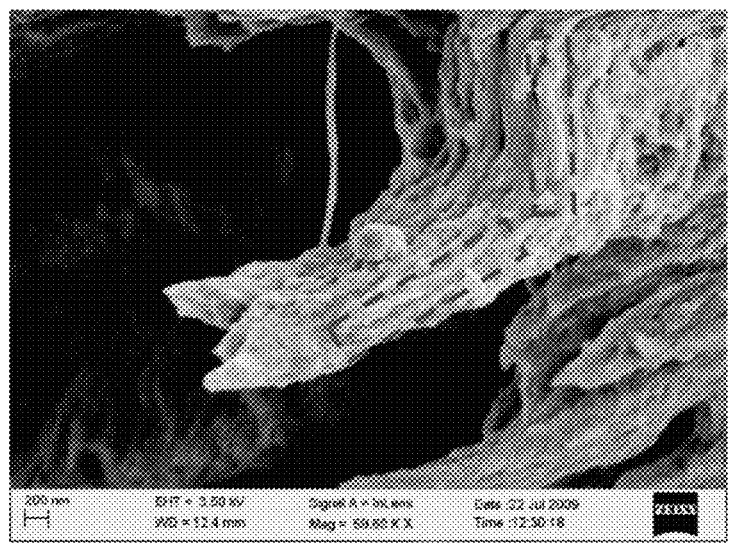
FIG. 2A is a scanning electron microscopy (SEM) photomicrograph of healthy bone tissue from a mouse showing typical elongated mineral crystal aligned longitudinally with regard to collagen.
Figure 2B:
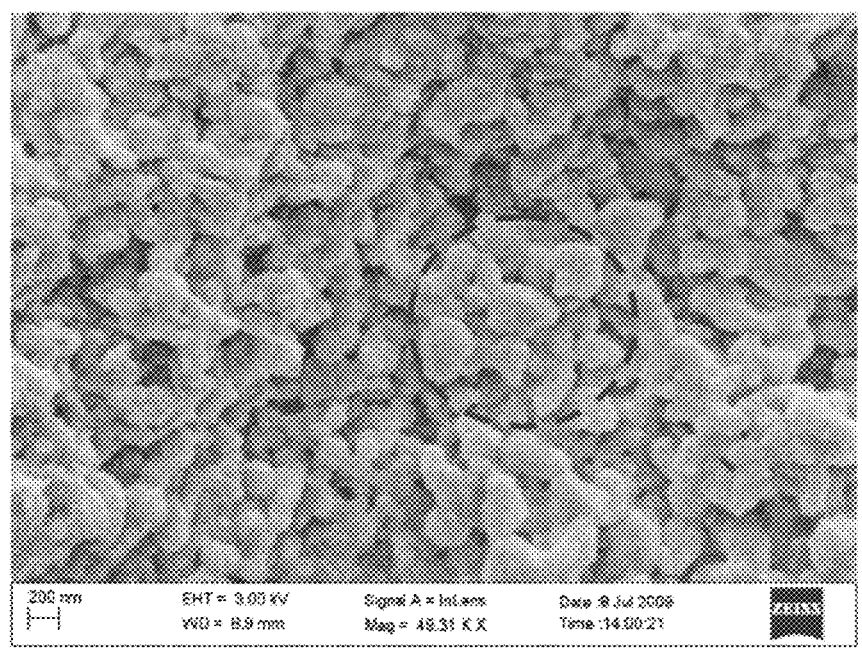
FIG. 2B is an SEM of mouse bone tissue lacking osteocalcin and osteopontin exhibiting circular and haphazardly arranged mineral crystals.

FIG. 2A is a scanning electron microscopy (SEM) photomicrograph of healthy bone tissue from a mouse showing typical elongated mineral crystal aligned longitudinally with regard to collagen. By comparison, FIG. 2B is an SEM of bone tissue from a double-knockout mouse lacking functional expression of osteocalcin and osteopontin, exhibiting circular and haphazardly arranged mineral crystals. Characterization of the mouse strains used is known from published literature. See, e.g., Nikel et al (2013) Langmuir 29:13873-13822. All measurements were done on cortical bone samples of WT, OC−/−. OPN−/− and OC−OPN−/−;−/− mice (n=4-5 each group). Small angle x-ray scattering (SAXS) spectra were obtained for each specimen (Bruker Nanostar) and numerically analyzed to obtain information on crystal size, shape and orientation according to known methods. Wavelength dispersive spectroscopy (WDS) enabled obtention of trace elemental composition for each specimen. WDS (Cameca SX-100 Electron Microprobe) was performed on carbon-coated cortical bone sections (5-10 data acquisition points per specimen).

Figure 3A:
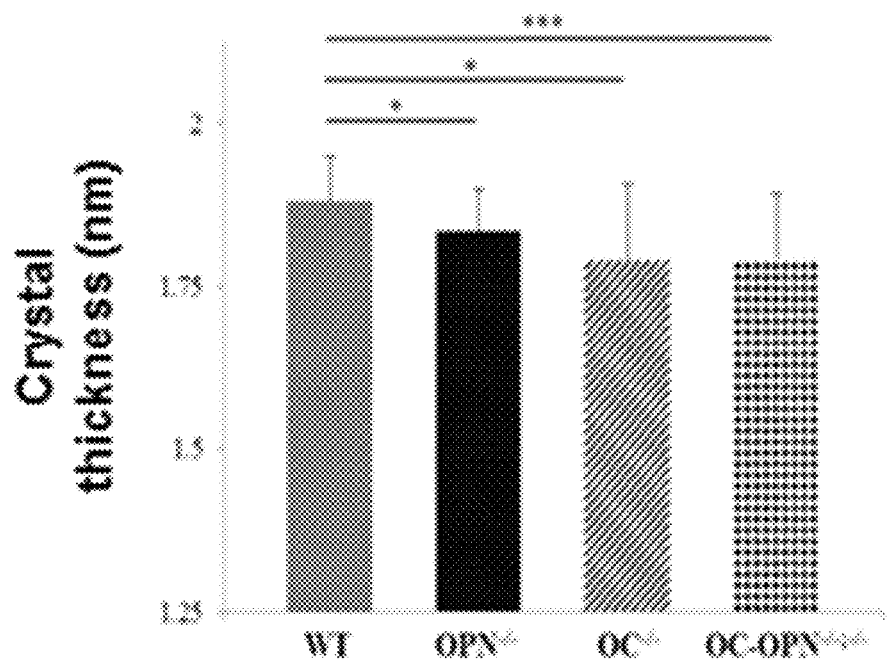
FIG. 3A is a bar graph showing differences in mineral crystal thickness (Y-axis) between bone tissue of wild-type mice (WT), mice lacking osteopontin (OPN), mice lacking osteocalcin (OC), or mice lacking OPN and OC.
Figure 3B:
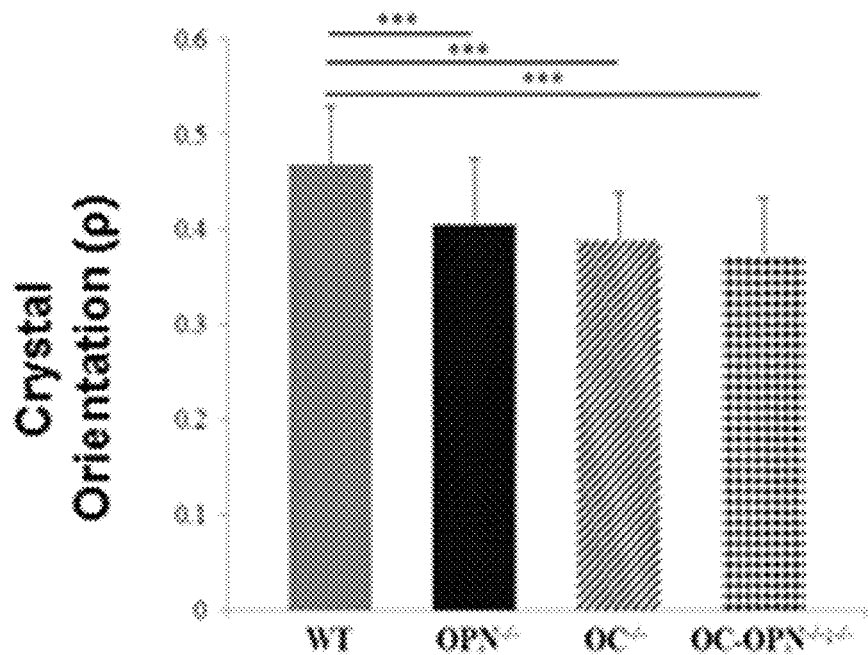
FIG. 3B is a bar graph showing differences in mineral crystal orientation (Y-axis) between bone tissue of wild-type mice (WT), mice lacking osteopontin (OPN), mice lacking osteocalcin (OC), or mice lacking OPN and OC.
Figure 3C:
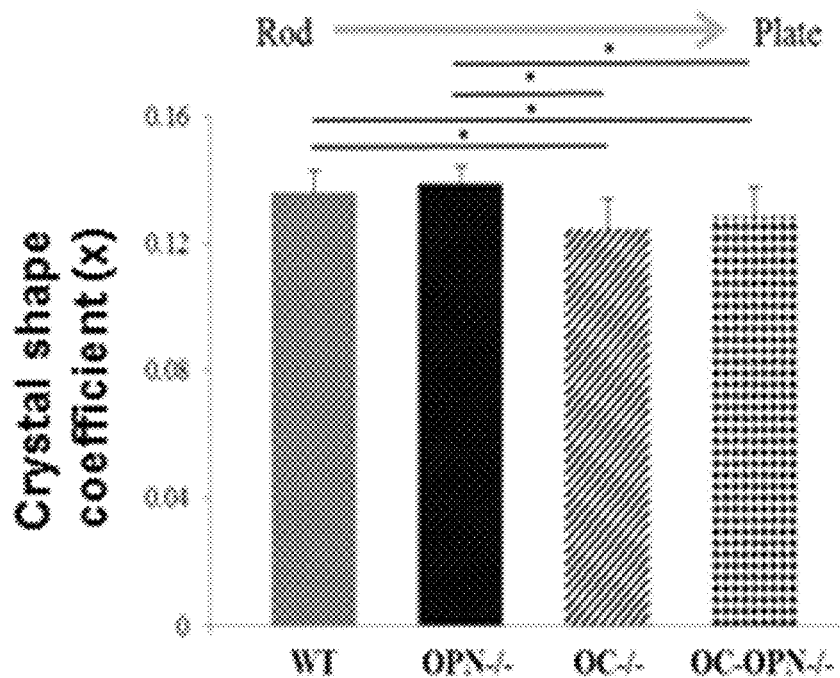
FIG. 3C is a bar graph showing differences in mineral crystal shape (Y-axis) between bone tissue of wild-type mice (WT), mice lacking osteopontin (OPN), mice lacking osteocalcin (OC), or mice lacking OPN and OC.
Figure 4A:
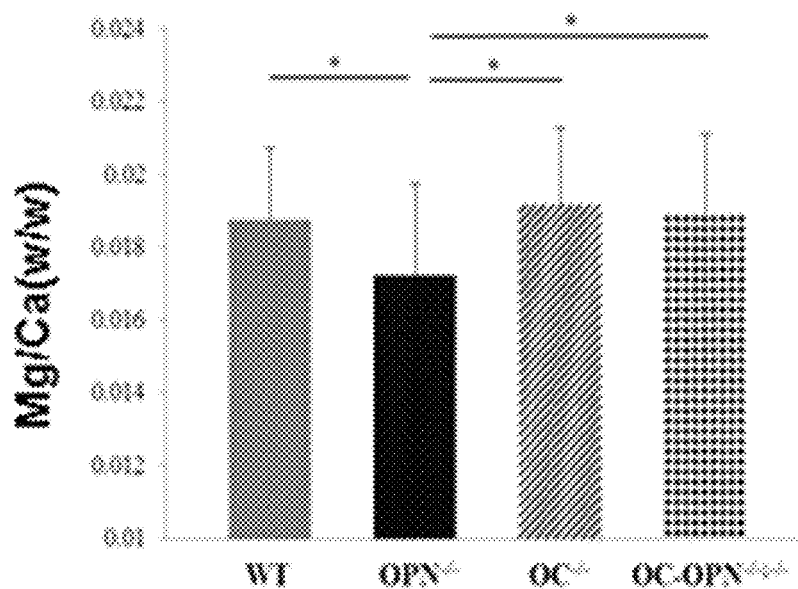
FIG. 4A, FIG. 4B, and FIG. 4C are bar graphs showing compositional differences in the amounts of trace elements Mg, F, and S, respectively, between bone tissue of wild-type mice (WT), mice lacking osteopontin (OPN), mice lacking osteocalcin (OC), or mice lacking OPN and OC.
Figure 4B:
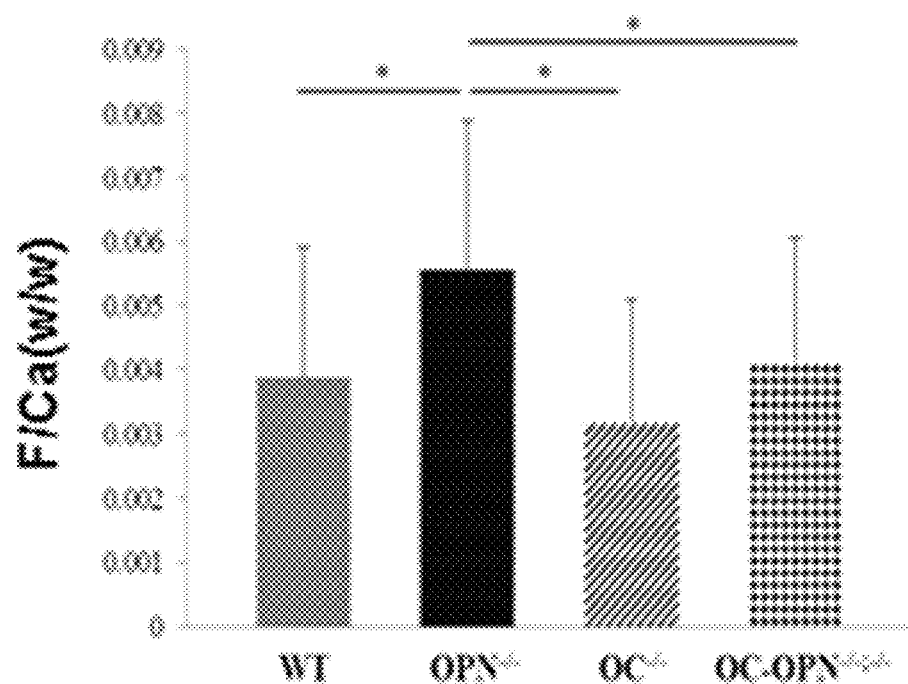
Figure 4C:
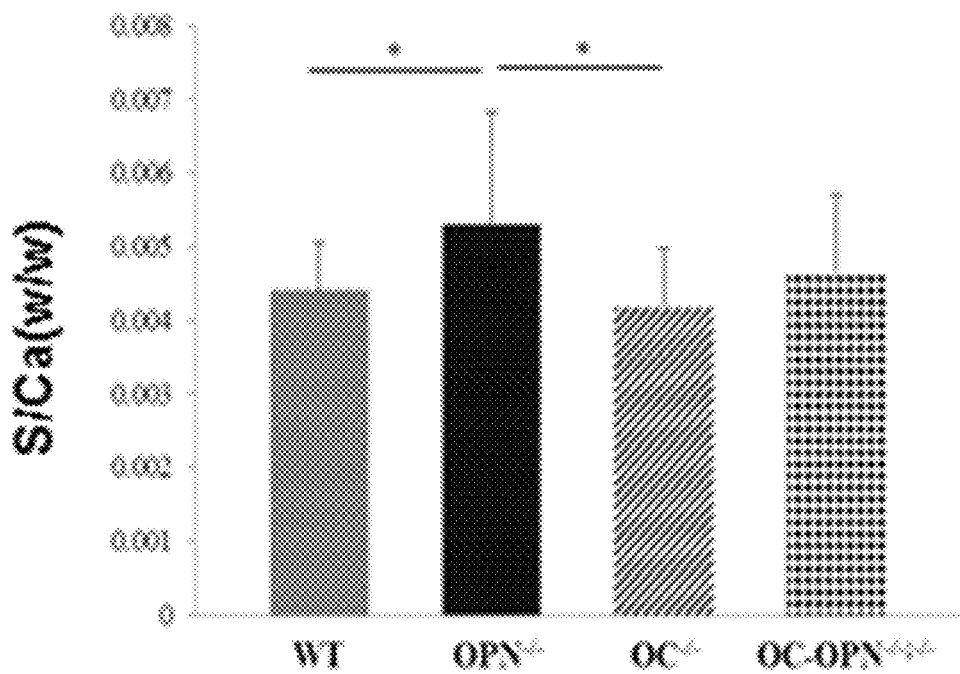

As shown in FIG. 3A, SAXS analysis demonstrated that OC is a stronger regulator of mineral crystal size and shape than OPN, and its absence in OC−/− and OC−OPN−/−;−/− bones reduces crystal dimensions by up to 15% when compared to WT with a 5% difference between means. As shown in FIG. 3B, degree of orientation of crystals (p) in WT mice was significantly greater than that in all the knock-out groups ($p<0.05$). As shown in FIG. 3C, OC−/− and OC−OPN−/−;−/− bones had more plate-like crystals as compared to WT and OPN−/− bones, where the shape was more elongated ($p<0.05$). WDS revealed that the absence of OPN resulted in ~10-35% compositional variation of trace elements (Mg, F and S shown in FIGS. 4A-4C) as compared to WT mice.

Altogether, the foregoing results demonstrate that OC and OPN regulate the nanoscale hierarchy and composition of bone matrix, play a prominent structural role in bone quality, and therefore aid the self-assembly process of bone mineral while tailoring the chemical and physical nature of the mineral that precipitates onto collagen. In accordance with the present invention, including OC and OPN in a graft provides a graft with a more natural material composition and topography than conventionally available bone grafts or substitutes. When mixed with a commercially available binder material, such as certain types of carrier, a graft can also be injected and molded into a site of injury or defect, for minimally invasive applications. Optionally, OC, OPN, or both may be subsequently removed leaving behind the formed mineralized graft (optionally including, for example, type-I collagen or a carrier) for implantation or other purposes.

Included in the present invention are a method for promoting tissue mineralization using a substance according to the present invention, such as but not limited to using a substance made according to the foregoing example, such a substance itself, a method of manufacturing such a substance, and an article for promoting tissue mineralization such an orthopedic or endosseous implant with such a substance disposed on its surface. According to another embodiment, a tissue mineralization-promoting substance may be made by contacting a solid template comprising type-I collagen with calcium, phosphate, OC, and OPN. For example, such components could be rendered in individual or combined solutions and applied to a type-I collagen-containing template. Such a template may be formed in any desired or advantageous shape or configuration appropriate for the intended site of tissue mineralization and/or bone grafting, repair, or regeneration. Articles or templates including these features promote bone regeneration, healing, and repair, and tissue mineralization, when disposed within the body of a subject. A substance may be so disposed as a coating on an implant or as part of a prefabricated template, or as a cement, gel, liquid, paste, or granular substance for introduction into a body. A result may be enhanced repair of damaged bone, replacement of lost bone, repair of joint tissue, repair of an interface between soft-tissue (cartilage, tendon, ligament) and bone, therapeutic fusion of bones, or better adhesion of an implant to endogenous bone.

In accordance with the present invention, a substance may promote tissue mineralization, bone repair, bone regeneration, bone replacement, therapeutic bone fusion, or adhesion of a template with endogenous bone when the substance includes OC, OPN, and a carrier. In accordance with the present invention, OC and OPN act synergistically to promote these functions and do not require the presence of exogenously provided collagen or calcium phosphate. A carrier may be included to promote delivery of tissue mineralization-promoting substance in accordance with the present invention. A method of making such a substance, similar to the non-limiting example described above but without certain features such as inclusion of calcium phosphate or other minerals or trace elements or type-I collagen, may be used, such as adding OC and OPN to a carrier. Such a substance may be placed within a body for promoting the therapeutic processed described above. Articles such as implants including such a substance may include such a substance. Such a substance may also be made by contacting a solid template with OC and OPN, such as, for example, disposing OC and OPN in solution on a solid template.

OC may be of mammalian origin, such as human, rat, mouse, or bovine, and may be obtained by purification from mammalian bone such as from human bone or from bovine bone, or may be synthesized recombinantly, by known methods. It is available commercially from vendors. In an example, mature OC peptide may be used, which may be isolated from tissue or artificially or recombinantly synthesized.

OPN may be of mammalian origin, such as human, rat, mouse, or bovine, and may be obtained by purification from mammalian bone such as from human bone or from bovine bone, or may be synthesized recombinantly, by known methods. It is available commercially from vendors. In an example, mature OPN peptide may be used, which may be isolated from tissue or artificially or recombinantly synthesized.

Type-I collagen may be of mammalian origin, such as human, rat, mouse, or bovine, and may be obtained by purification from mammalian bone such as from human bone or from bovine bone, or may be synthesized recombinantly, by known methods. It is available commercially from vendors. In an example, mature type-I collagen peptide may be used, which may be isolated from tissue or artificially or recombinantly synthesized.

EXAMPLES

The following examples are intended to illustrate particular embodiments of the present invention, but in no way limit the scope of the present invention.

Figure 5:
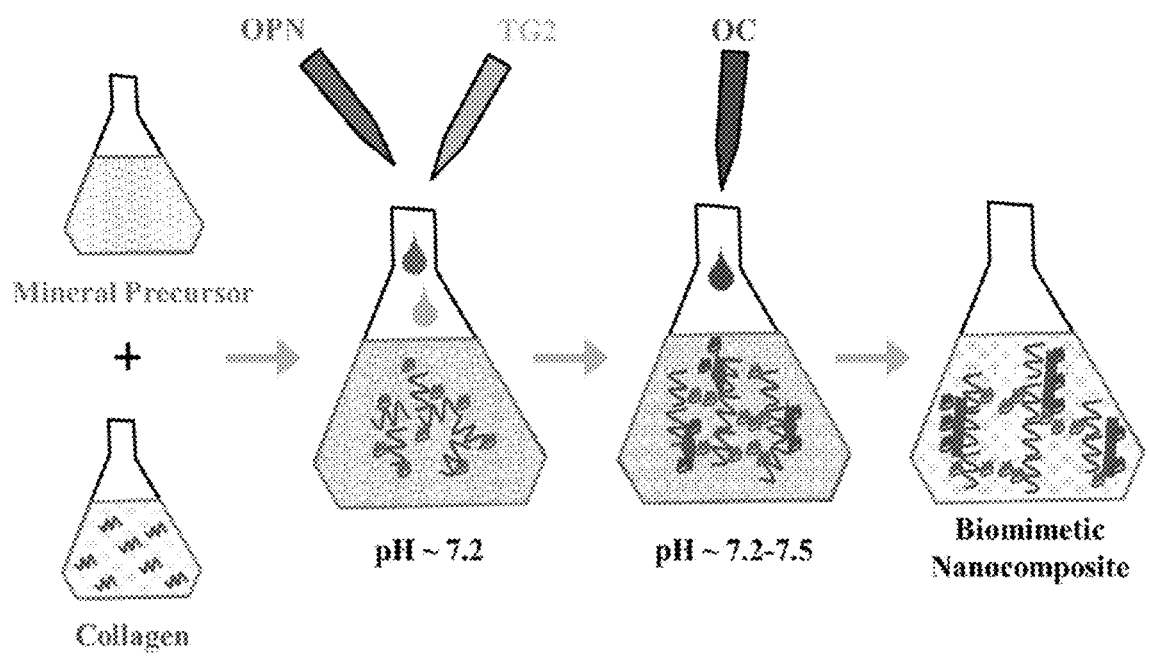
FIG. 5 is a schematic drawing of one embodiment of an aspect of the invention according to which a bone mineralization-promoting substance may be made.

FIG. 5 is a diagrammatic representation of one, non-limiting example of a method for forming a tissue mineralization-promoting substance in accordance with the present invention, as explained in the following.

Bone mineral or hydroxyapatite (HA), may contain impurities within the crystal lattice. Impurities that exist as anions like carbonate, fluoride and chloride, substitute the hydroxyl or phosphate sites within the HA lattice. Cationic impurities such as trace elemental ions (for example, $Mg^{2+}$, $Na^+$, $Zn^{2+}$, etc.), may substitute for calcium sites within the HA lattice. The presence of impurities may increase the solubility of HA and enhance bone formation. Additionally Mg and other trace elements may promote bone health. Magnesium, shown to be abundant in precursor elements of bone mineral during the mineralization process in vivo, may enhance HA formation in vivo.

As shown in a representative example shown in FIG. 5, a mineral precursor solution of calcium phosphate and exemplary trace elements magnesium (Mg), sodium (Na), strontium (Sr), fluorine (F) and sulfur (S) may be made. A mineral precursor solution may itself be created by combining separate solutions containing different mineral components (e.g., a calcium chloride solution and a sodium phosphate solution), as would be readily appreciated by those who have skill in the relevant field. This solution will act as a basis for a mineral component of a biomimetic nanocomposite in accordance with the present invention. Other elements like iron (Fe), zinc (Zn), selenium (Se), or others, or subcombinations of any of the foregoing, also may be incorporated within the precursor solution, to tailor the chemistry of the mineral phase and affect the response of bone cells in vivo.

The weight fraction of mineral in bone depends on the level of mineralization. Fully mineralized human bone contains 40%-70% mineral by weight, the rest being organic matrix, principally collagen. For some applications, a bone mineralizing substance including 40%-70% by weight mineral may be advantageous, whereas for other applications, using lower (20%-40%) or higher (70%-80%) mineral weight proportions may be better suited to a given application. In accordance with the present invention, mineralization may be tailored by, for example, altering the fraction of mineral in the starting mineral precursor solution. The amounts of trace elements can also be varied within the following range (all percent values are represented as molar fraction of total calcium present):

Magnesium (Atomic Wt.=24.3 gm)~1-8%
Sodium (Atomic Wt.=23 gm)~2-15%
Fluorine (Atomic Wt.=19 gm)~0.2-4%
Chlorine (Atomic Wt.=35.45 gm)~0.1-2%
Sulfur (Atomic Wt.=32 gm)~0.1-2.5%
Carbonate (Molecular Wt.=60 gm) 1.5-3%
Other trace elements like Zn, Fe, Si etc.<0.1%

All the species mentioned above may be added to the precursor solution as inorganic compounds such as oxide, carbonates or fluorides in a combination such that the totals for each lies within the above range. As an example, magnesium sulfide, magnesium carbonate, sodium chloride, sodium carbonate and sodium fluoride may be used; other combinations can used to arrive at the molar ratios calculated above.

Calcium constitutes 40% by weight of hydroxyapatite. So 3 gm of HA used as starting material contains ~1.2 gm of Ca by weight (0.03 mol). In one example, 0.017 gm MgS (~1% Mg and 1% S or 0.0003 mol), 0.0253 gm $MgCO_3$ (~1% Mg and 1% $CO_3^{2-}$), 0.0175 gm NaCl (~1% Na and 1% Cl), 0.0249 gm $Na_2CO_3$ (~2% Na and 1% $CO_3^{2-}$) and 0.0126 gm NaF (~1% Na and 1% F) are combined. In this example, the total trace element/impurity composition per mole of calcium is: Mg—2%, Na—4%, F—1%, Cl—1%, S—1% and $CO_3^{2-}$—2%, i.e. within the ranges specified above. HA and trace element compounds may then be dissolved in 0.5 N HCl to form a saturated solution referred to as a mineral precursor solution.

In another aspect, an acidic solution of collagen type-I may be obtained. Collagen type-I (human, bovine or porcine) is readily available commercially, and can be purchased either as lyophilized powder or a dilute solution. An acidic solution may be made by dissolving lyophilized collagen powder in 0.01-0.1 M HCl, at room temperature. Alternatively, a dilute solution of collagen may also be used (1-10 mg/ml). When using the powder form, dilution of the collagen should be minimized. The amount of collagen powder needed for a graft may be arrived at based on percent mineralization to be achieved, and the weight of mineral component used (i.e. if a final mineralization of 60% needs to be achieved and total weight of the mineral component used is 3 gm, the corresponding organic content (40%) equals 2 gm).

NaOH is added gradually to an acidic precursor solution, to raise the pH of the mixture. This titration step is carried out at room temperature. Concentrated NaOH (~1M) may be used to raise pH to approximately 6.0, so that dilution of the precursor solution is minimized. When the pH is within the 6-7 range, the collagen solution may be gradually mixed with the mineral solution and titration with NaOH is continued, using lower concentrations (0.1-0.001M) to prevent the pH from going above 7.0. PBS (1×) can also be used instead of dilute NaOH.

Tissue transglutaminase 2 (TG2) is a well-known cross-linking enzyme and has been proven efficacious and safe in the food industry to bind meat together. As a non-limiting example of the present invention, TG2 may be employed to crosslink collagen and OPN. Crosslinking type-I collagen and osteopontin using TG2 will create a nucleation template for hydroxyapatite to grow on. (Optionally or alternatively, OC may also be cross-linked to collagen.) As pH of the collagen-mineral mixture rises to and above 7, OPN and TG2 are added to the solution. Both OPN and TG2 are available in powder form and may be dissolved in 1×PBS prior to addition. OPN concentration may range from 0.01-2 mg/gm of the substance and a concentration of 0.5-0.5 mg/ml may be used. A ratio of TG2 to OPN (by weight) may be varied from 0.1 to 10. Addition of OPN and TG2 may be in a slow continuous manner, over a period of 1-5 hours at 37° C., while pH is maintained at ~7.2. OPN and TG2 may be dissolved in PBS and titrated against the precursor solution in a drop wise manner. At this pH, some turbidity may be visible and indicates that mineral and collagen have begun to precipitate. Maintaining pH<7.2 prevents all the collagen/mineral from precipitating out of the solution, before OPN and collagen are sufficiently cross-linked.

After the addition of OPN and TG2, pH of the mixture is raised and maintained between 7.2-7.5 throughout the rest of the process. The temperature of the solution is kept at 37° C. OC may be added in a manner similar to addition of OPN and TG2. OC (0.01-3 mg/gm of graft material) may first be dissolved in PBS and added drop wise over the next few hours (1-5 hrs). In accordance with the present invention, OC plays a significant role in growth and maturation of mineral crystals in bone and, in particular, a tissue mineralization-promoting substance. Once nucleated in the presence of cross-linked OPN and collagen, the presence of OC helps direct the growth and direction of mineral crystals during the self-assembly process. This self-assembly and mineralization process is allowed to progress over the next day (24 hrs) until no further precipitation (as checked by turbidity measurements) is detectable.

The foregoing example is but one, non-limiting embodiment of a method for synthesizing a tissue mineralization-promoting substance. As described above, different features or aspects of this example may be modified, removed, or added to, within the present invention.

Figure 6:
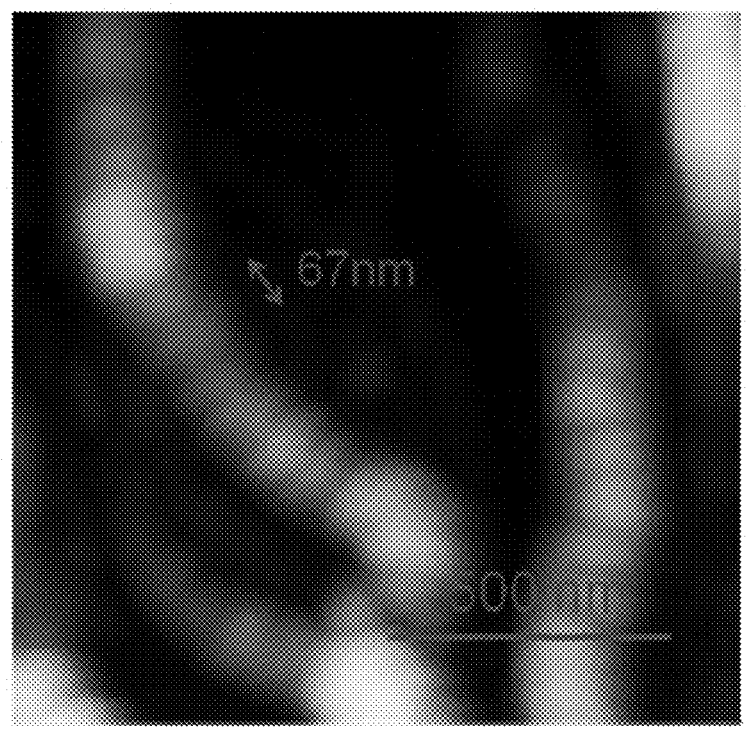
FIG. 6 is an atomic force microscopy (AFM) image of type-I collagen fibrils which were self-assembled in accordance with an aspect of one embodiment of the present invention.
Figure 7:
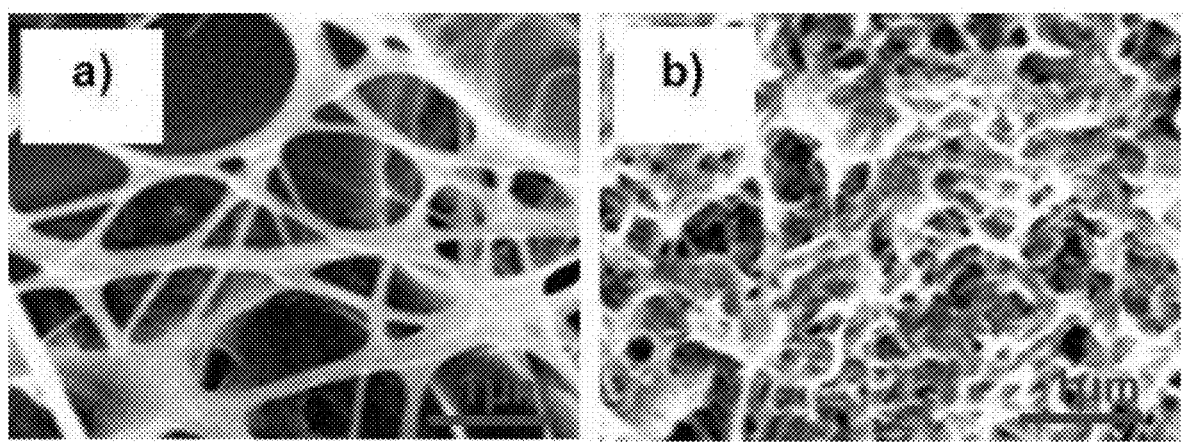
FIG. 7 shows an SEM photomicrograph of bovine type-I collagen fibrils self-assembled in presence of OPN (left), and an SEM photomicrograph of mineralization on the self-assembled collagen-OPN matrix (right), in accordance with an aspect of one embodiment of the present invention.

In another non-limiting example, type-I collagen fibrils were synthesized in accordance with a method of the present invention by which a tissue mineralization substance is made (i.e., combining type-I collagen, calcium phosphate, OC, and OPN). FIG. 6 is an atomic force microscopy (AFM) image of resulting, self-assembled collagen fibrils. Type-I collagen were assembled in vitro using dissolved rat tail collagen (BD Biosciences) fibrils and displayed a ~100 nm width and 67 nm D-periodicity banding pattern characteristic of collagen in bone. The ability to achieve collagen D-periodicity may promote mineral nucleation. Collagen assembly was also carried out in the presence of physiological concentrations of phosphorylated bovine OPN (Sigma Aldrich, Sigma-03514) and the matrix was mineralized using co-precipitation of calcium chloride and sodium phosphate (Sigma Aldrich). In an example, recombinantly synthesized mature human OC was commercially obtained (Sigma; Cat #05761) and recombinant human OPN was obtained commercially (R&D Systems, Cat #1433-OP-050/CF). Electron microscopy revealed the formation of fibrous collagen network (FIG. 7, left) and biomimetic plate-like or flaky mineral formation (FIG. 7, right). The present invention therefore synthesizes mineral akin to both natural bone and octacalcium (OCP)-citrate, recently postulated to be present in natural bone. In another embodiment, mineral may be deposited on a prefabricated collagen scaffold template, using precursor mineral solutions containing osteocalcin/osteopontin and strontium chloride.

Figure 8:
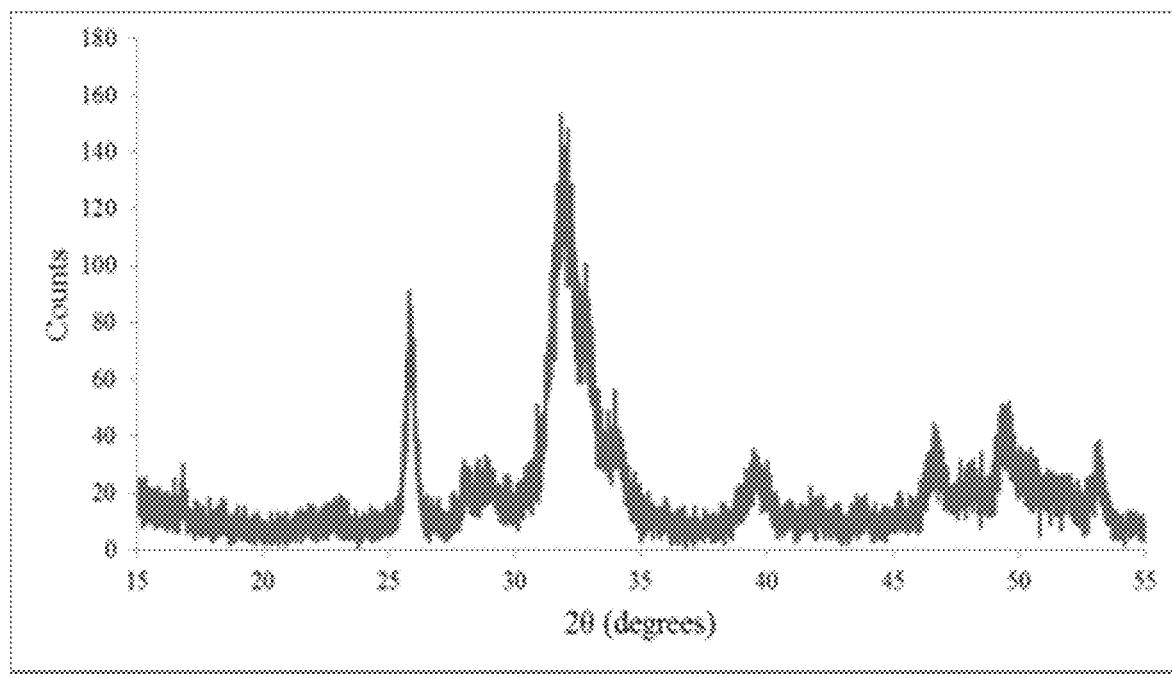
FIG. 8 is a graph showing X-ray diffraction characterization of bone mineral, synthesized in vitro at room temperature in accordance with an aspect of one embodiment of the present invention.

Mineral was synthesized in accordance with the present invention, at room temperature in vitro, and characterized using x-ray diffraction. FIG. 8 is a graph showing X-ray diffraction characterization of bone mineral synthesized in accordance with an aspect of the present invention. These x-ray diffraction data closely resembles the X-ray diffraction characterization of octacalcium (OCP)-citrate and bone as demonstrated in publicly available literature, demonstrating the effectiveness of the present invention in fabricating a tissue mineralization-promoting substance that induces physiological mineralization processes. See Davies et al. (2014) Proceedings of the National Academy of Sciences, 111, E1354-E1363.

Demineralization of allografts to obtain demineralized bone matrix (DBM) products has previously been reported to leach out bone morphogenetic proteins (BMP) into the 0.6M HCl demineralization solution. Presently, defatted and powdered human bone samples were demineralized in 0.6N HCl at 4° C. for a period of 6 hours according to known methods. Glycerol and protease inhibitors were added to ensure de-agglomeration and prevent degradation of the eluted proteins respectively. The supernatant and precipitate were quantitatively tested for the presence of osteocalcin through an antibody based ELISA assay. 52% of bone's osteocalcin is lost from DBM during the HCl demineralization process. Given the importance of OC in promoting healthy bone formation demonstrated herein, tissue mineralizing substances in accordance with the present invention exhibit a marked improvement over conventional sources of bone-regenerative substances such as DBM.

In another non-limiting example, collagen may be a delivery vehicle for a bioactive mixture (OPN and OC), concentrating the bioactive agent at a localized site of administration and controlling the release of the bioactive composition. A bioactive component of a substance includes OPN and OC. In an example, OPN was administered in a concentration ranging from 0 µg to 0.3 µg for each 100 µl of collagen type I (3 mg/ml) and OC was administered in a concentration ranging from 0 µg to 1.2 µg for each 100 µl of collagen type I (3 mg/ml).

In an example, OC purified from bovine bone was obtained commercially (Millipore; Cat. #499050) and OPN, purified from bovine milk, was obtained commercially (R&D Systems; Cat. #109-OP-050/CF). Different concentrations of OC and OPN were applied. The addition of OPN and OC alone was tested, such that different concentrations of OC and OPN were combined into a delivery system based into collagen gels.

In vitro 3D collagen type I matrix is a convenient system that allows for the mimicking of in vivo 3D extracellular matrix (ECM) of connective tissue, where collagen type I is a predominant ECM molecule. In vitro 3D fibrillar collagen matrix is a meshwork of collagen fibrils polymerized from collagen molecules or monomers. Collagen fibril formation occurs when soluble collagen is brought to physiological conditions of neutral pH (around 7.4-7.8) and warmed to 20-37° C. In one example, a concentration of collagen monomers used to polymerize fibrillary collagen networks determined density of matrix and pore size. Collagen density between 1 and 3 mg/ml may be used to prepare collagen gels, allowing cell transmigration through pores in the matrix. Alternatively, a pre-fabricated matrix may be purchased commercially. (Other examples of suitable carriers are described above.) If a collagen network is dense, it can be difficult for cells to navigate through the matrix and it may be advantageous to employ proteases to cleave collagen fibrils, facilitating the squeezing of the cell body through pores, and/or, use pore-forming agents known in the art.

The following compositions of OC and OPN were evaluated: 0.3 µg OC/0.06 µg OPN (#1), 0.3 µg OC/0.3 µg OPN (#2), 0.3 µg OC/0.012 µg OPN (#3), 1.2 µg OC/0.06 µg OPN (#4), 0.075 µg OC/0.06 µg OPN (#5), 0 µg OC/0 µg OPN (control), 0.3 µg OC/OPN (#6) and 0 µg OC/0.06 µg OPN (#7). These different conditions of concentrations of OC and OPN were added to a purified bovine collagen I solution at 3 mg/ml. After incubation overnight at 37° C., collagen gels enriched with these proteins were formed.

Human bone marrow mesenchymal stem cells (hMSC) (A15653, Life Technologies) were seeded at 10,000 cells/cm2 into each collagen gel (3000 cells each) using MesenPRO RS Medium (Life Technologies). After 24 hours, the medium was removed and osteogenic medium (Life Technologies) was replaced to provide osteogenesis differentiation of hMSC. Cultures were maintained at 37° C. in a humidified incubator supplemented with 5% CO2. Medium was changed every 2-3 days. The collagen gels were cultured for 28 days. After 5, 10, 15 and 21 days, proliferation and mineralization assays were performed.

PrestoBlue cell viability reagent (LifeTechnologies) was used to evaluate cell proliferation. PrestoBlue reagent is a resazurin based solution and was used as a cell viability indicator. The Presto Blue reagent contains a cell permeant compound that is blue in color and virtually nonfluorescent. When added to cells, the PrestoBlue reagent is modified by the reducing environment of the viable cells turning red in color and becoming highly fluorescent. This change was detected quantifying the fluorescence of each sample using a plate reader. Cell proliferation was measured in triplicates in all groups.

One indicator of human MSC differentiation is calcium deposition, which was quantified using a commercial calcium assay kit (StanbioTotal Calcium LiquiColor, Stanbio Laboratory). The procedure presented is based on a method where calcium is disassociated from proteins in an acidic solution, followed by its direct reaction with ortho-cresolphthalein complexone (OCPC). In a subsequent alkaline medium the Ca-OCPC complex forms a purple color, which is then measured at 550 nm. The amount of calcium in the sample is proportional to the color development in the reaction. Briefly, calcium-containing supernatant from human MSC culture was mixed with the working reagent, incubated for 5 minutes, and the absorbance was read at 550 nm using a plate reader. After 21 days, proliferation assay suggests that human MSCs demonstrated a higher increase in fluorescence when seeded into collagen gels supplemented with both osteocalcin and osteopontin, suggesting that the combination of osteocalcin and osteopontin has a significant influence in proliferation of hMSC in collagen gels. See FIG. 9A.

Figure 9A:
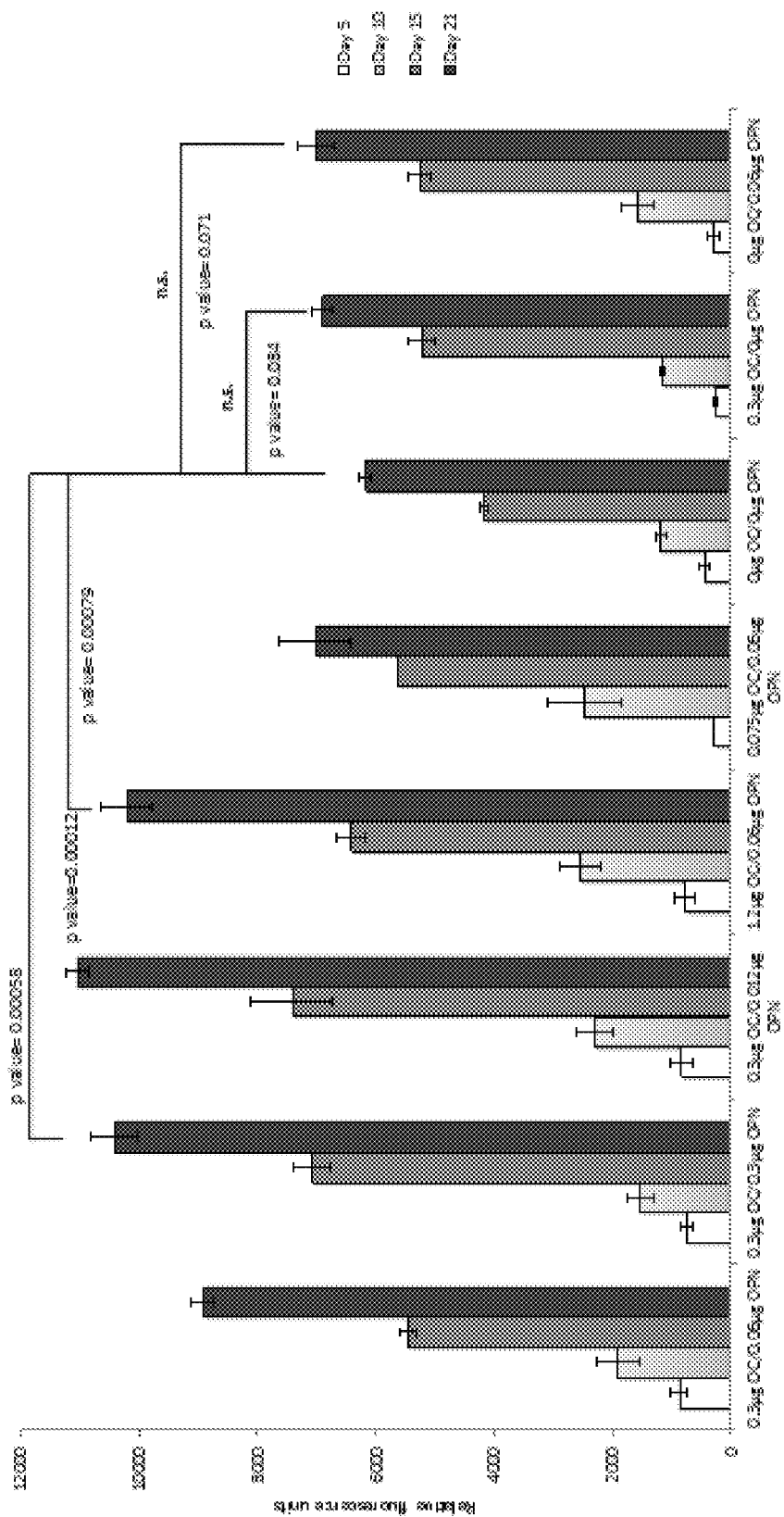
FIG. 9A shows levels of human bone marrow mesenchymal stem cell proliferation (Y axis) following incubation in vitro with different concentrations of osteocalcin (OC; 0-1.2 μg/100 μl) and osteopontin (OPN; 0-0.3 μg/100 μl) for 5, 10, 15, and 21 days.

As shown in FIG. 9A, after 21 days in culture, collagen gels supplemented with 0.3 µg OC/0.012 µg OPN (#3) demonstrated a significant increase of fluorescence of, approximately, 65% compared with the control collagen gels (without any protein supplementation) (fluorescence of 10213 compared to a fluorescence of 6181 for control group) (p-value of 0.00012). However, after 21 days, hMSC seeded on collagen gels supplemented only with OC or only with OPN did not demonstrate a significant increase in proliferation, suggesting that osteocalcin and osteopontin act in synergy.

Figure 9B:
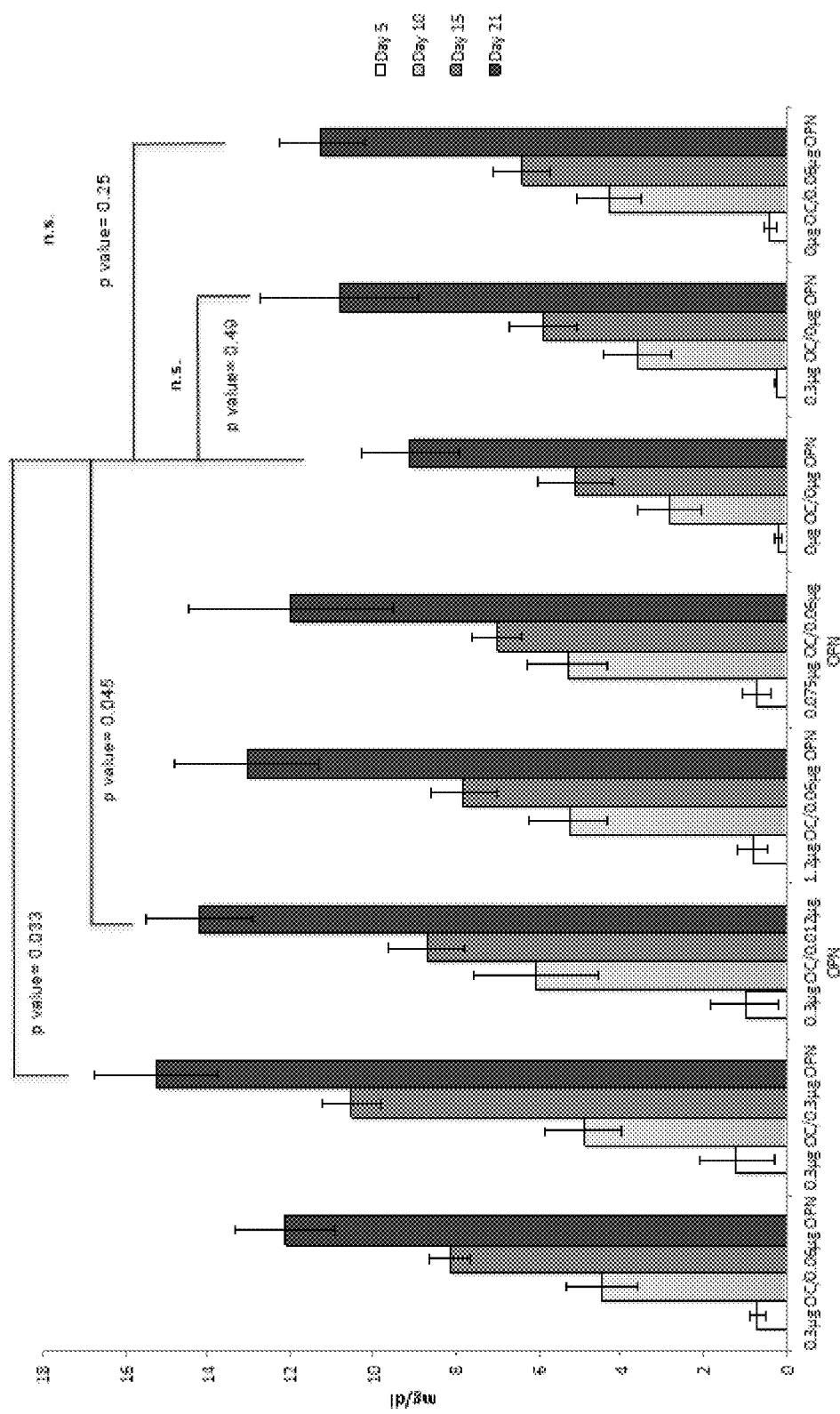
FIG. 9B shows levels calcium deposition by osteoblasts that have differentiated from bone marrow mesenchymal stem cell (Y axis) following incubation in vitro with different concentrations of osteocalcin (OC; 0-1.2 μg/100 μl) and osteopontin (OPN; 0-0.3 μg/100 μl) for 5, 10, 15, and 21 days.

Calcium deposition by human MSC is an important indicator of osteogenic differentiation. As shown in FIG. 9B, after 21 days of differentiation, no statistically significant difference in calcium deposition was detected between collagen gels (control—without osteocalcin and osteopontin) and collagen gels supplemented only with osteocalcin or only with osteopontin (0.3 µg OC/0 µg OPN (#6) and 0 µg OC/0.06 µg OPN (#7)). However, when a combination of OC and OPN was incorporated into the collagen gels, the average calcium deposition per collagen gel was greater than the control (collagen gels without any protein) and gels with only OC or only OPN.

After 21 days of differentiation, collagen gels supplemented with 0.3 µg OC/0.012 µg OPN demonstrated a significant increase (p-value of 0.045) of calcium deposition of 56% compared with the collagen gels without any protein supplementation (14.2 mg/dl compared with 9.1 mg/dl) and collagen gels supplemented with 0.3 µg OC/0.3 µg OPN demonstrated a significantly increase (p-value of 0.033) of calcium deposition of 68% compared with the collagen gels without any protein supplementation (15.2 mg/dl compared with 9.1 mg/dl).

These results demonstrate that OC and OPN, used in accordance with the present invention, have an unexpected and surprising synergistic effect on proliferation and mineralization of collagen gels. Furthermore, effectiveness of OC and OPN in combination without addition of exogenous mineral components and resulting in increased proliferation of mesenchymal stem cells demonstrates a surprising, synergistic biological effect of OC and OPN separate and distinct from their roles in promoting mineral crystal nucleation, crystal growth, and crystal conjugation. The present invention includes adopting the use of OC and OPN, together with other innovative compositions and in methodologically innovative ways, to promote tissue mineralization.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed. Where a description herein of an embodiment or example recites that such embodiment or example "may" possess a certain feature, characteristic, aspect, or element, the term "may" indicates that such feature, characteristic, aspect, or element is optional and need not be included in every embodiment or example of an invention as disclosed herein.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of one or more aspects of the invention and the practical application, and to enable others of ordinary skill in the art to understand one or more aspects of the invention for various embodiments with various modifications as are suited to the particular use contemplated.

What is claimed is:

1. An article comprising:
   an orthopedic implant including a surface; and
   a coating disposed on the surface, the coating including a tissue mineralization-promoting substance,
   wherein the substance includes type I collagen, calcium phosphate, osteopontin, osteocalcin, and a compound that removes advanced glycation endproducts (AGEs),
   wherein the concentration of osteopontin in the substance is about 0.06 µg and the concentration of osteocalcin in the substance is about 0.3 µg,
   wherein at least one of a plurality of osteopontin molecules are enzymatically cross-linked to type-I collagen.

2. The article of claim 1, wherein calcium phosphate is selected from the group consisting of monocalcium phosphate monohydrate, monocalcium phosphate anhydrous, dicalcium phosphate dihydrate, dicalcium phosphate anhydrous, octacalcium phosphate, α-tricalcium phosphate, β-tricalcium phosphate, amorphous calcium phosphate, calcium-deficient hydroxyapatite, hydroxyapatite, fluorapatite, tetracalcium phosphate, and any combination of two or more of the foregoing.

3. The article of claim 1, comprising a scaffold and a plurality of cells disposed on the scaffold wherein the plurality of cells is selected from the group consisting of osteoblasts, osteoclasts, fibroblasts, mesenchymal stem cells, embryonic stem cells, and any combination of two or more of the foregoing.

4. The article of claim 1, further comprising one or more compounds selected from the group consisting of magnesium, sodium, fluorine, chlorine, sulfur, zinc, iron, silicon, selenium, strontium, copper, lithium, nickel, manganese, barium, phosphorous, aluminum, cobalt, titanium, vanadium, and any combination of two or more of the foregoing.

5. The article of claim 1, wherein at least one of a plurality of osteocalcin molecules is enzymatically cross-linked to type-I collagen and at least one of a plurality of osteopontin molecules is enzymatically cross-linked to osteocalcin.

6. The article of claim 1, further comprising one or more growth factors selected from the group consisting of a platelet-derived growth factor, a bone morphogenetic protein, an insulin-like growth factor, a transforming growth factor-β, a vascular endothelial growth factor, a fibroblast growth factor, and any combination of two or more of the foregoing.

7. The article of claim 1, comprising a proportion by weight of collagen of between 20% and 80% and a proportion by weight of calcium phosphate of between 20% and 80%.

8. The article of claim 1, further comprising citrate.

* * * * *